(12) United States Patent
Beer et al.

(10) Patent No.: US 8,765,455 B2
(45) Date of Patent: *Jul. 1, 2014

(54) CHIP-BASED DROPLET SORTING

(75) Inventors: Neil Reginald Beer, Pleasanton, CA (US); Abraham Lee, Irvine, CA (US); Andrew Hatch, Irvine, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 13/014,792

(22) Filed: Jan. 27, 2011

(65) Prior Publication Data

US 2012/0196288 A1     Aug. 2, 2012

(51) Int. Cl.
*C12M 3/00*     (2006.01)
(52) U.S. Cl.
USPC ........................................... 435/287.2

(58) Field of Classification Search
None
See application file for complete search history.

(56) References Cited

U.S. PATENT DOCUMENTS

2007/0284254 A1*  12/2007  Cho et al. .................... 204/547
2008/0166793 A1*  7/2008  Beer et al. .................. 435/287.2

FOREIGN PATENT DOCUMENTS

WO     WO 2008/082432 A1     7/2008

OTHER PUBLICATIONS

Ramadan et al. (2006) Sensors and Actuators B 113 pp. 944-955.*

* cited by examiner

*Primary Examiner* — Suchira Pande
(74) *Attorney, Agent, or Firm* — Eddie E. Scott

(57) ABSTRACT

A non-contact system for sorting monodisperse water-in-oil emulsion droplets in a microfluidic device based on the droplet's contents and their interaction with an applied electromagnetic field or by identification and sorting.

2 Claims, 10 Drawing Sheets

CHIP-BASED DROPLET SORTING

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to droplet sorting and more particularly to chip-based droplet sorting.

2. State of Technology

Microfluidic devices are poised to revolutionize environmental, chemical, biological, medical, and pharmaceutical detectors and diagnostics. "Microfluidic devices" loosely describes the new generation of instruments that mix, react, count, fractionate, detect, and characterize complex gaseous or liquid-solvated samples in a micro-electro-mechanical system (MEMS) circuit manufactured through standard semiconductor lithography techniques. These techniques allow mass production at low cost as compared to previous benchtop hardware. The applications for MEMS devices are numerous, and as diverse as they are complex.

As sample volumes decrease, reagent costs plummet, reactions proceed faster and more efficiently, and device customization is more easily realized. By reducing the reaction volume, detection of target molecules occurs faster through improved sensor signal to noise ratio over large, cumbersome systems. However, current MEMS fluidic systems may only be scratching the surface of their true performance limits as new techniques multiply their sensitivity and effective throughput by ten, a hundred, or even a thousand times.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a unique non-contact system for sorting monodisperse water-in-oil emulsion droplets in a microfluidic device based on the droplet's contents and their interaction with an applied electromagnetic field or by identification and sorting. The system allows for individual droplets in a continuous stream to be selected based on optical methods and then sorted to a different channel or to be sorted without optical detection by the interaction of the droplets and their contents with an applied alternating electromagnetic field. The system also provides for the fabrication of the array of electrodes that allow selection and diversion of one or more droplets from a continuous-flowing stream, and can be coupled to other on-chip processes to increase device efficiency by sorting out un-reacted droplets.

The present invention has use in identifying, detecting, and monitoring bio-threat agents that contain nucleic acid signatures, such as spores, bacteria, viruses etc. The present invention also has biomedical applications for tracking, identifying, and monitoring outbreaks of infectious disease including emerging, previously unidentified and genetically engineered pathogens; automated processing, amplification, and detection of host or microbial and viral DNA or RNA in biological fluids for medical purposes; high throughput genetic screening for drug discovery and novel therapeutics; genetic screening for oncology, disease, and personal genomics; compound discovery, proteomics, crystallography, and other research applications Forensic applications; and automated processing, amplification, and detection DNA in biological fluids for forensic purposes.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
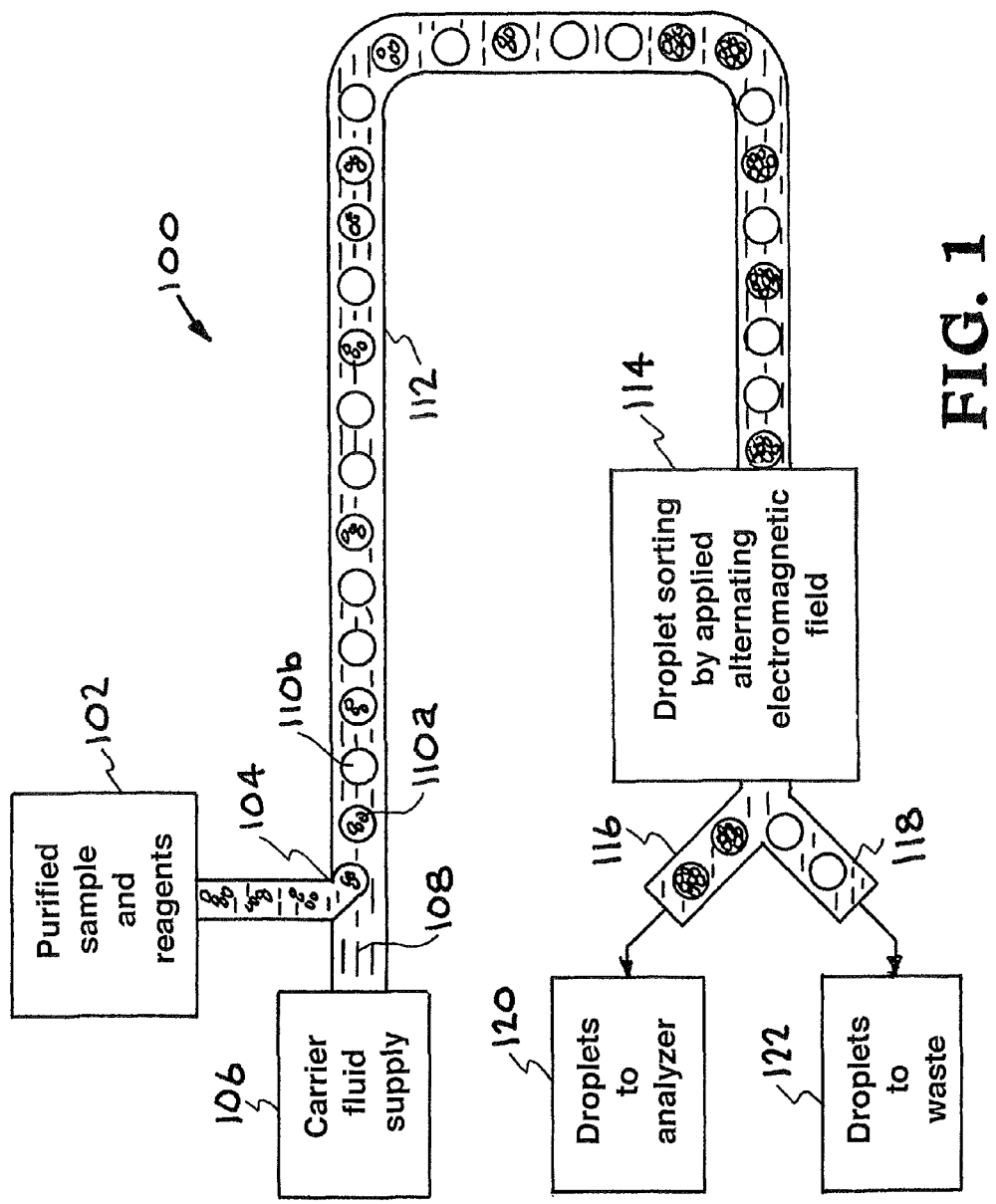
FIG. 1 illustrates one embodiment of a system for generating and sorting microdroplets containing a sample.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a unique non-contact method and apparatus for isolating and sorting monodisperse water-in-oil emulsion droplets in a microfluidic device based on the droplet's contents and their interaction with an applied electromagnetic field. The method and apparatus allows for individual droplets in a continuous stream to be selected based on optical methods and then sorted to a different channel or to be sorted without optical detection by the interaction of the droplets and their contents with an applied alternating electromagnetic field. The method and apparatus also provide for the fabrication of an array of electrodes that allow selection and diversion of one or more droplets from a continuous-flowing stream, and can be coupled to other on-chip processes to increase device efficiency by sorting out un-reacted droplets.

Referring now to the drawings and in particular to FIG. 1, one embodiment of a system for generating and sorting microdroplets containing a sample is illustrated. The system illustrated in FIG. 1 includes the following structural elements: microfluidic device 100, a source 102 of the sample and reagents, a droplet maker 104, a source 106 of carrier fluid, the carrier fluid 108, micro droplets containing a material 110a, empty micro droplets that do not containing the material 110b, a main microfluidic flow channel 112, a droplet sorter 114, a separator channel 116, a separator channel 118, an analyzer 120, and waste 122. The droplet maker 104 illustrated in FIG. 1 produces droplets by a shearing action. It is to be understood that other apparatus and methods of forming droplets can be used. For example, droplets can be produced by flow focusing and acoustic apparatus and methods.

The system provides generation of a monodisperse stream of microdroplets 110a and 110b and subsequent sorting of the droplets based on the droplet's contents and their interaction with an applied electromagnetic field in the droplet sorter 114. The microfluidic device 100 provides a system for sorting droplets of varying contents which also affect their dielectric permittivity. This can include but is not limited to PCR amplification, cell encapsulation, crystallization, chemical reactions and polymerizations, and other droplet streams of mixed content.

The microfluidic device 100 is an apparatus for sorting droplets that includes a main flow channel 112; a carrier fluid 108 in the main flow channel 112; a droplet maker 104 connected to the main flow channel 112 that provides a flow stream of droplets 110a, 110b in the main flow channel 112 wherein the droplets have substantially the same diameter and wherein the droplets include first droplets 110a containing a material and second droplets 110b that do not contain the material; an analyzer 120; a waste channel 122; and a droplet sorter 114 that sorts the droplets according to the first droplets 110a containing the material and directs the first droplets 110a containing the material to the analyzer 120 and sorts the droplets according to the second droplets 110b that do not contain the material and directs the second droplets 110b that do not contain the material to the waste channel 122. The first droplets 110a contain a material. The material may be genetic material, PCR amplification material, cell encapsulation, crystallization, chemical reactions and polymerizations, and other droplet streams of mixed content.

As illustrated in FIG. 1, the system and method for sorting droplets includes a number of individual steps for sorting droplets. In step one purified sample and reagents 102 are carried to step two where droplet formation 104 occurs. Droplets of uniform size are formed during step two and enter the main flow channel 112. The main flow channel 112 is filled with a carrier fluid 108 that does not mix with the droplets 110a, 110b therefore the droplets are carried along in main flow channel 112 at spaced intervals. Some of the droplets contain material and some droplets are empty. The droplets proceed along the main flow channel 112 to step three where droplet sorting by (AC-DEP) alternating current dielectrophoresis 114 occurs. After step four the (AC-DEP) sorting the droplets 110a containing the material of interest will go by way of channel 116 to the droplet analyzer 120 and the empty droplets 110b will travel in channel 118 to the droplet waste 122.

Figure 2:
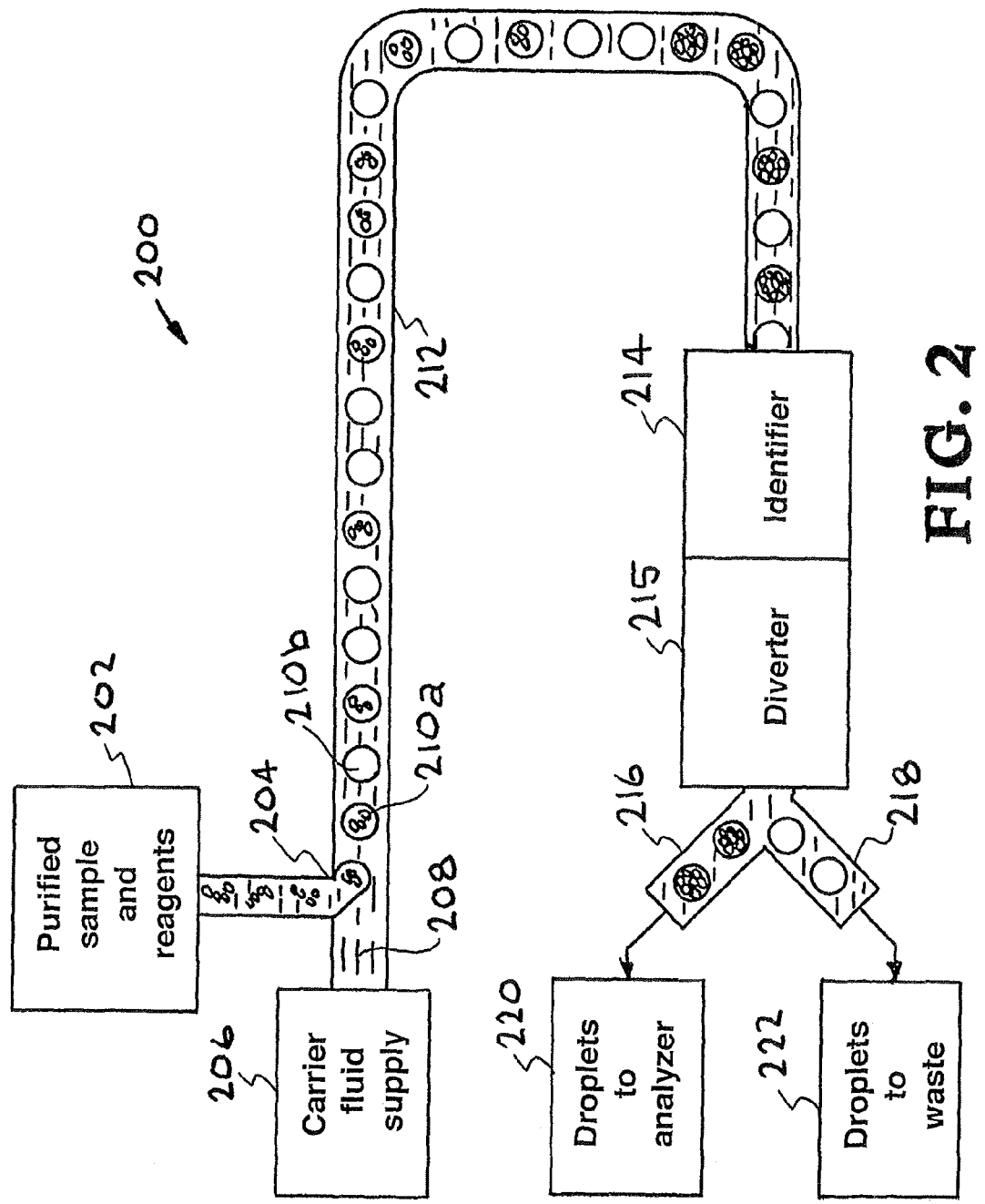
FIG. 2 illustrates another embodiment of a system for generating and sorting microdroplets containing a sample.

Referring now to FIG. 2, another embodiment of a system for generating and sorting microdroplets containing a sample is illustrated. The system illustrated in FIG. 2 includes the following structural elements: microfluidic device 200, a source 202 of the sample and reagents, a droplet maker 204, a source 206 of carrier fluid, the carrier fluid 208, micro droplets containing a material 210a, empty micro droplets that do not containing the material 210b, a main microfluidic flow channel 212, a droplet identifier 214, a droplet diverter 215, a separator channel 216, a separator channel 218, an analyzer 220, and waste 222. The system provides generation of a monodisperse stream of microdroplets 210a and 210b and subsequent sorting of the droplets based on the droplet's contents and their interaction with the droplet identifier 214 and the droplet diverter 215. The microfluidic device 200 provides a system for sorting droplets of varying contents which also affect their dielectric permittivity. This can include but is not limited to PCR amplification, cell encapsulation, crystallization, chemical reactions and polymerizations, and other droplet streams of mixed content.

The microfluidic device 200 is an apparatus for sorting droplets that includes a main flow channel 212; a carrier fluid 208 in the main flow channel 212; a droplet maker 204 connected to the main flow channel 212 that provides a flow stream of droplets 210a, 210b in the main flow channel 212 wherein the droplets have substantially the same diameter and wherein the droplets include first droplets 210a containing a material and second droplets 210b that do not contain the material; an analyzer 220; a waste channel 222; and the droplet identifier 214 and the droplet diverter 215, that sorts the droplets according to the first droplets 210a containing the material and directs the first droplets 210a containing the material to the analyzer 220 and sorts the droplets according to the second droplets 210b that do not contain the material and directs the second droplets 210b that do not contain the material to the waste channel 222. The first droplets 210a contain a material. The material may be genetic material, PCR amplification material, cell encapsulation, crystallization, chemical reactions and polymerizations, and other droplet streams of mixed content.

As illustrated in FIG. 2, the system and method for sorting droplets includes a number of individual steps for sorting droplets. In step one purified sample and reagents 202 are carried to step two where droplet formation 204 occurs. Droplets of uniform size are formed during step two and enter the main flow channel 212. The main flow channel 212 is filled with a carrier fluid 208 that does not mix with the droplets 210a, 210b therefore the droplets are carried along in main flow channel 212 spaced intervals. Some of the droplets contain material and some droplets are empty. The droplets proceed along the main flow channel 212 to step three where droplet sorting by interaction with the droplet identifier 214 and the droplet diverter 215 occurs. After step four the sorting the droplets 210a containing the material of interest will go by way of channel 216 to the droplet analyzer 220 and the empty droplets 210b will travel in channel 218 to the droplet waste 222.

Figure 3:
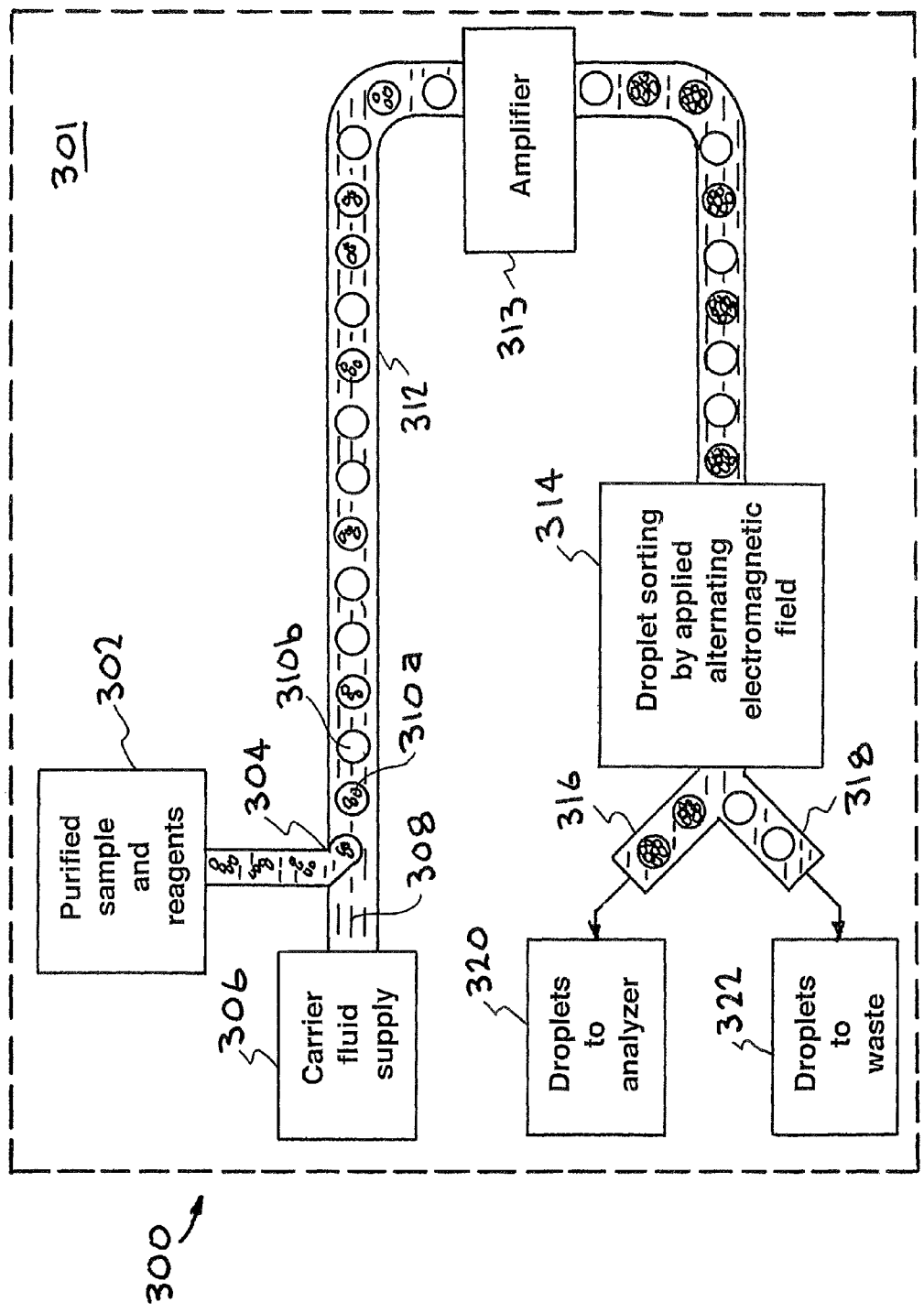
FIG. 3 illustrates yet another embodiment of a system for generating and sorting microdroplets containing a sample.

Referring now to FIG. 3, another embodiment of a system for generating and sorting microdroplets containing a sample is illustrated. The system illustrated in FIG. 3 includes the following structural elements: microfluidic device 300, chip 301, a source 302 of the sample and reagents, a droplet maker 304, a source 306 of carrier fluid, the carrier fluid 308, micro droplets containing genetic material 310a, empty micro droplets that do not containing the material 310b, a main microfluidic flow channel 312, an amplifier 313 for amplifying the genetic material, a droplet sorter 314, a separator channel 316, a separator channel 318, an analyzer 320, and waste 322. The system provides generation of a monodisperse stream of microdroplets 310a and 310b, amplifying the genetic material in droplets 310a using amplifier 313, and subsequent sorting of the droplets based on the droplet's contents and their interaction with an applied electromagnetic field in the droplet sorter 314. The microfluidic device 300 provides a system for sorting droplets of varying contents which also affect their dielectric permittivity.

The microfluidic device 300 is an apparatus for sorting droplets on a chip 301 that includes a main flow channel 312; a carrier fluid 308 in the main flow channel 312; an amplifier, 313, a droplet maker 304 connected to the main flow channel 312 that provides a flow stream of droplets 310a, 310b in the main flow channel 312 wherein the droplets have substantially the same diameter and wherein the droplets include first droplets 310a containing genetic material and second droplets 310b that do not contain the material; an analyzer 320; an amplifier 313 for amplifying the genetic material in droplets 310a producing amplified genetic material in droplets 310a, a waste channel 322; and a droplet sorter 314 that sorts the droplets according to the first droplets 310a containing the genetic material and directs the first droplets 310a containing the genetic material (amplified) to the analyzer 320 and also sorts the droplets according to the second droplets 310b that do not contain the genetic material and directs the second droplets 310b that do not contain the genetic material to the waste channel 322.

As illustrated in FIG. 3, the system and method for sorting droplets includes a number of individual steps for sorting droplets. In step one purified sample and reagents 302 are carried to step two where droplet formation 304 occurs. Droplets of uniform size are formed during step two and enter the main flow channel 312. The main flow channel 312 is filled with a carrier fluid 308 that does not mix with the droplets 310a, 310b therefore the droplets are carried along in main flow channel 312 spaced intervals. Some of the droplets, 310a, contain genetic material and some droplets, 310b, are empty. The genetic material in the first droplets is amplified by amplifier 313 producing droplets 310a, with amplified genetic material. The droplets proceed along the main flow channel 312 to step three where droplet sorting by (AC-DEP) alternating current dielectrophoresis 314 occurs. After step four the (AC-DEP) sorting the droplets 310a containing the genetic material (amplified) of interest will go by way of channel 316 to the droplet analyzer 320 and the empty droplets 310b will travel in channel 318 to the droplet waste 322.

Figure 4:
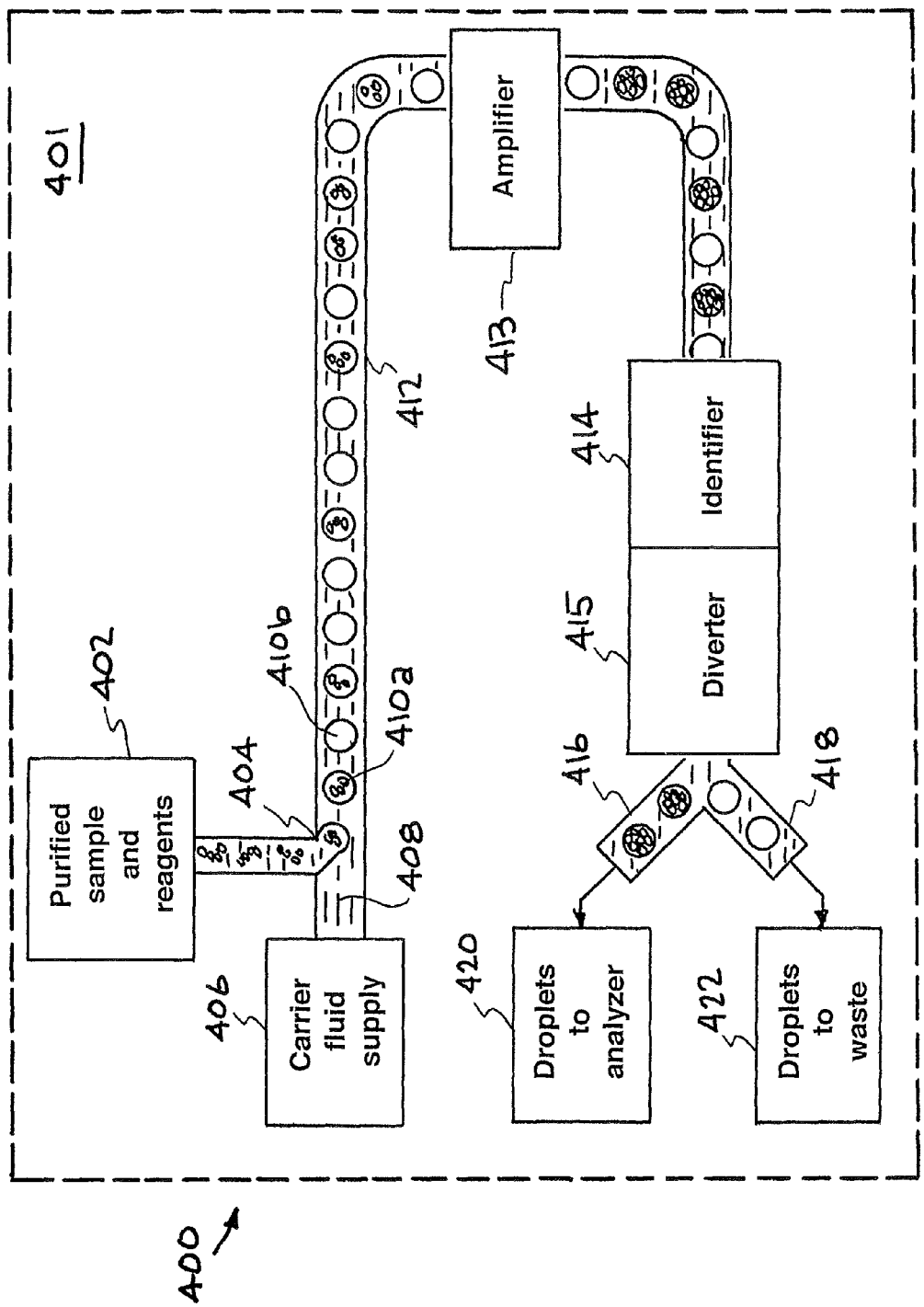
FIG. 4 illustrates embodiment of a system for generating and sorting microdroplets containing a sample.

Referring now to FIG. 4, another embodiment of a system for generating and sorting microdroplets containing a sample is illustrated. The system illustrated in FIG. 4 includes the following structural elements: microfluidic device 400, chip 401, a source 402 of the sample and reagents, a droplet maker 404, a source 406 of carrier fluid, the carrier fluid 408, micro droplets containing genetic material 410a, empty micro droplets that do not containing the material 410b, a main microfluidic flow channel 412, an amplifier 413 for amplifying the genetic material, a droplet identifier 414, a droplet diverter 415, a separator channel 416, a separator channel 418, an analyzer 420, and waste 422. The system provides generation of a monodisperse stream of microdroplets 410a and 410b, amplifying the genetic material in droplets 410a using amplifier 413, and subsequent sorting of the droplets based on the droplet's contents and their interaction with an applied electromagnetic field in the droplet sorter 414. The microfluidic device 400 provides a system for sorting droplets of varying contents.

The microfluidic device 400 is an apparatus for sorting droplets on a chip 401 that includes a main flow channel 412; a carrier fluid 408 in the main flow channel 412; an amplifier, 413, a droplet maker 404 connected to the main flow channel 412 that provides a flow stream of droplets 410a, 410b in the main flow channel 412 wherein the droplets have substantially the same diameter and wherein the droplets include first droplets 410a containing genetic material and second droplets 410b that do not contain the material, an analyzer 420, an amplifier 413 for amplifying the genetic material in droplets 410a producing amplified genetic material in droplets 410a, a waste channel 422; and a droplet identifier 414 and a droplet diverter 415. The droplet identifier 414 and a droplet diverter 415 sort the droplets according to the first droplets 410a containing the genetic material and directs the first droplets 410a containing the genetic material (amplified) to the analyzer 420 and also sorts the droplets according to the second droplets 410b that do not contain the genetic material and directs the second droplets 410b that do not contain the genetic material to the waste channel 422.

As illustrated in FIG. 4, the system and method for sorting droplets includes a number of individual steps for sorting droplets. In step one purified sample and reagents 402 are carried to step two where droplet formation 404 occurs. Droplets of uniform size are formed during step two and enter the main flow channel 412. The main flow channel 412 is filled with a carrier fluid 408 that does not mix with the droplets 410a, 410b therefore the droplets are carried along in main flow channel 412 spaced intervals. Some of the droplets, 410a, contain genetic material and some droplets, 410b, are empty. The genetic material in the first droplets is amplified by amplifier 413 producing droplets 410a, with amplified genetic material. The droplets proceed along the main flow channel 412 to step three where droplet sorting by droplet identifier 414 and a droplet diverter 415 occurs. After step four, the sorting the droplets 410a containing the genetic material (amplified) of interest will go by way of channel 416 to the droplet analyzer 420 and the empty droplets 410b will travel in channel 418 to the droplet waste 422.

Figure 5A:
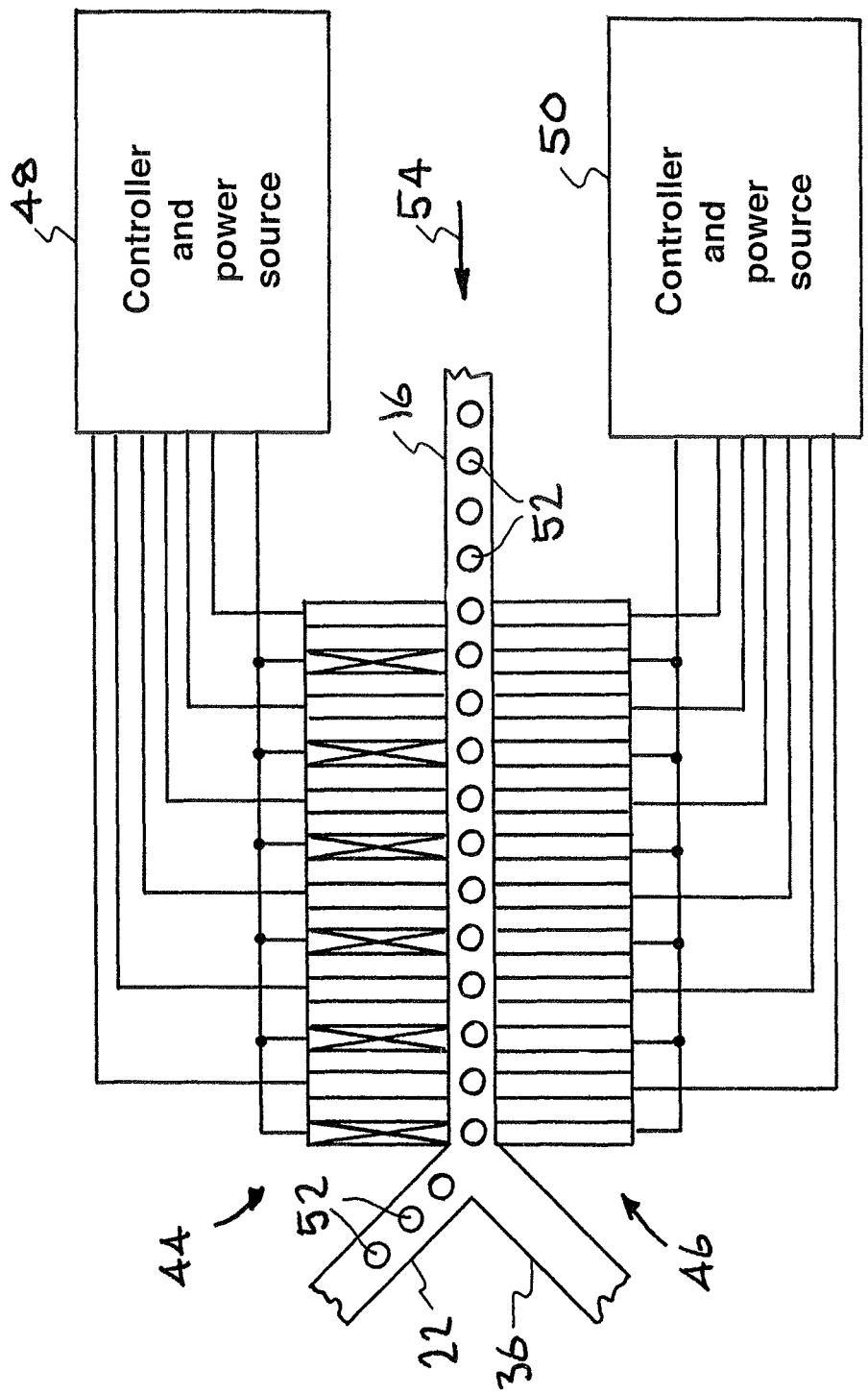
FIGS. 5A, 5B, and 5C illustrate how the alternating current dielectrophoresis (AC-DEP) tunes the DEP forces on a droplet by varying the frequency of activation for a given field gradient.
Figure 5B:
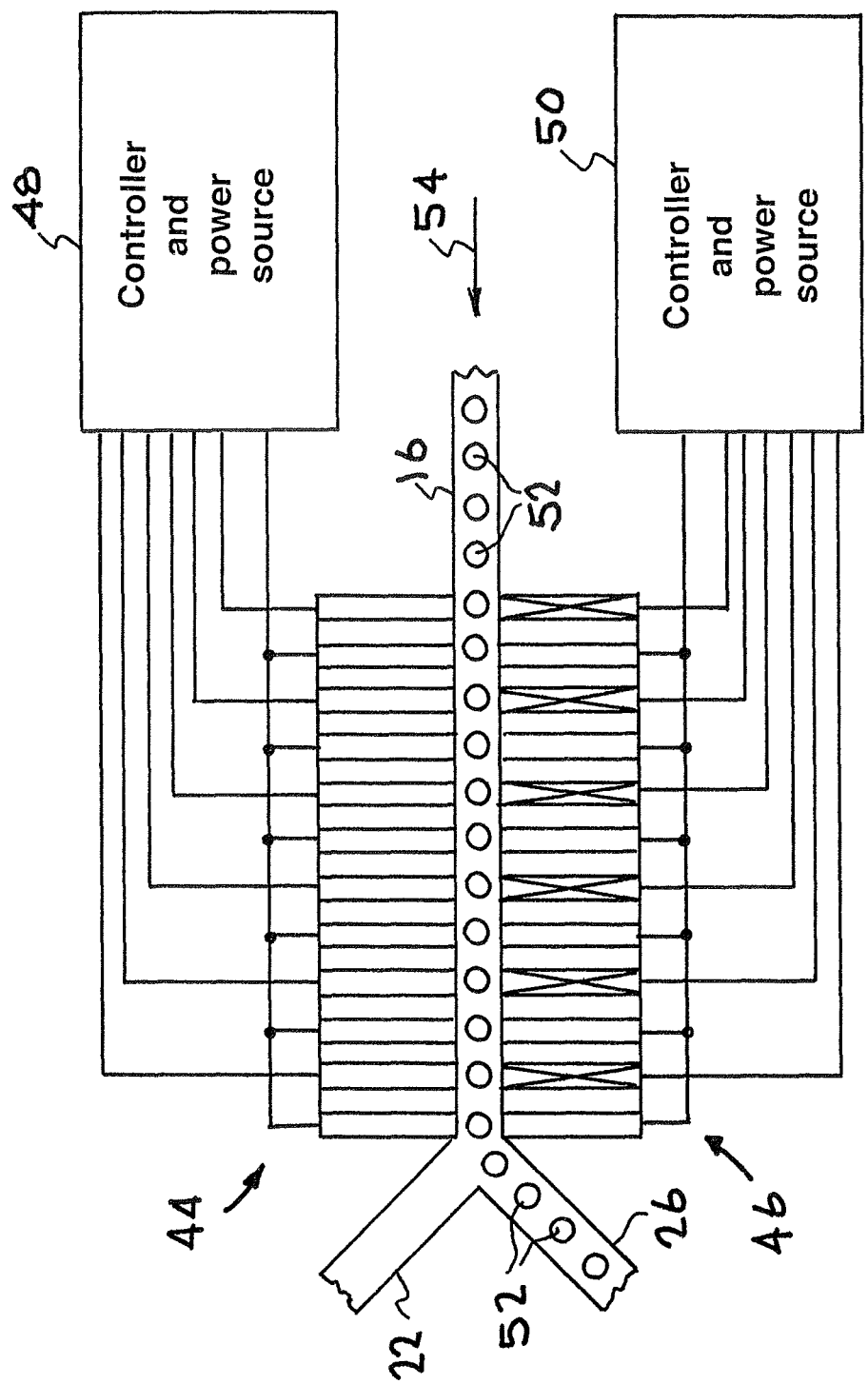
Figure 5C:
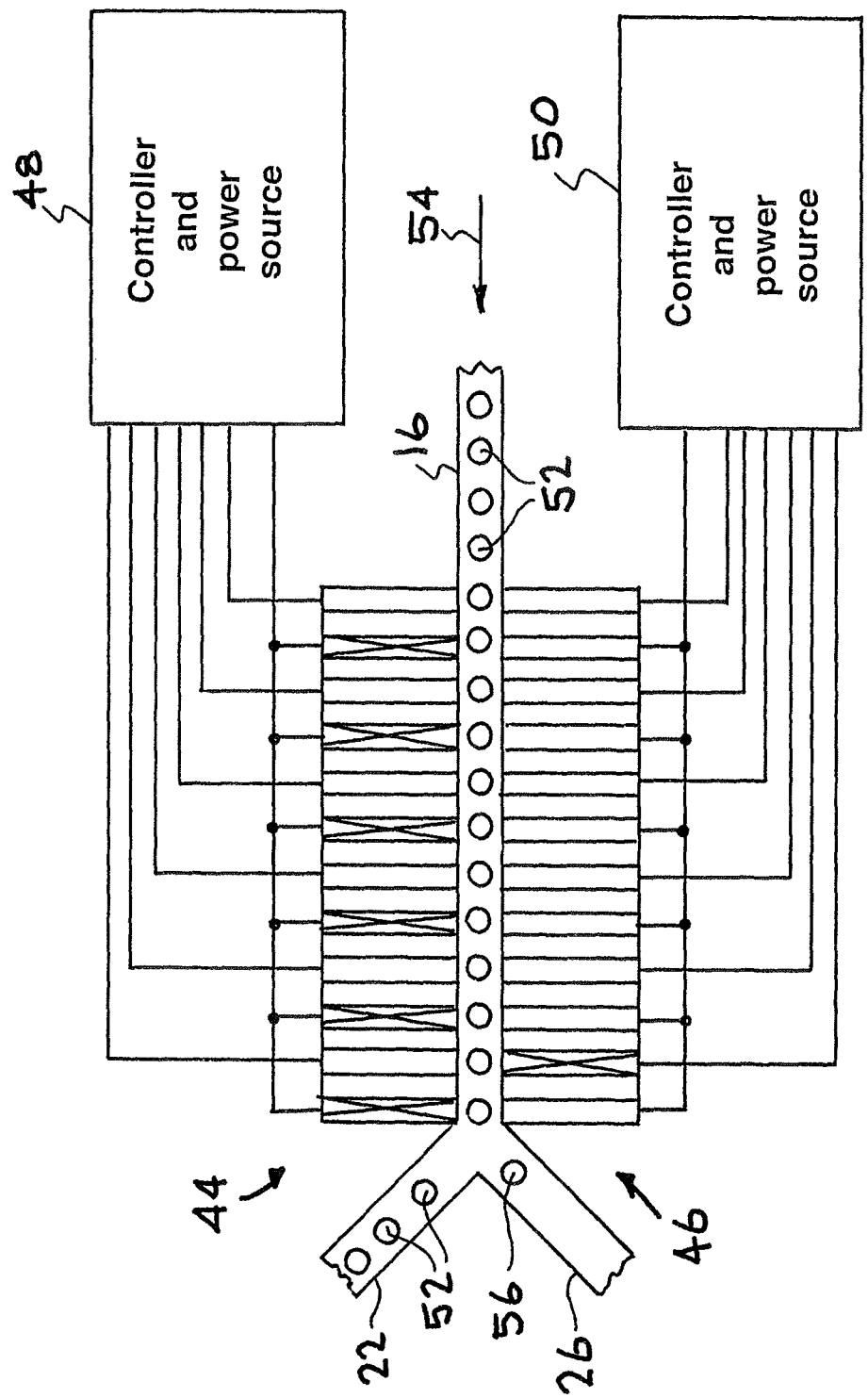

FIGS. 5A, 5B & 5C illustrate how the alternating current dielectrophoresis (AC-DEP) allows one to tune the DEP forces on a droplet by varying the frequency of activation for a given field gradient. To establish the desired field gradient acting along the desired length of a channel for active DEP sorting we use inter-digitated electrodes lining both sides of the channel 16. FIG. 5A shows the droplets 52 flowing along the channel 16 in the direction of arrow 54. By the controller 48 activating the electrode array 44 and assuming the attractive or positive DEP force the droplets will enter the channel 22. In FIG. 5B the electrode array 46 has been activated by the controller 50 causing the droplets 52 to veer into the channel 26. FIG. 5C shows that by selectively activating electrodes of the arrays 44 and 46 droplets can be isolated as shown by the droplet 56 entering channel 26. In the absence of any DEP activation, droplets will exit either channel outlet with equal distribution. By programming the controllers 48 and 50 a large verity of configurations for the electrode arrays 44 and 46 can be achieved.

Alternating current dielectrophoresis (AC-DEP) allows one to tune the active DEP forces on a droplet by varying the frequency of activation for a given electric field gradient. To establish the desired field gradient acting along the desired length of a channel for active DEP sorting we use inter-digitated electrodes which line the side channel walls on both sides. As seen in the top view diagrams below, activation of the bottom set of electrodes pulls droplets downward, and activation of top electrodes pulls the droplets in the opposite direction assuming an attractive or positive DEP force. In the absence of any DEP activation, droplets exit either channel outlet with equal distribution.

Utilizing a quick (50 ms) relaxation of electrode activation results in a single droplet being directed toward the collection channel while all other droplets are directed toward the waste channel (FIG. 2).

Depending on the AC frequency of electric field strength used, the magnitude and even the direction of the DEP forces exerted on a droplet can be tuned according to its complex dielectric permittivity. The governing equations used to describe the complex dielectric permittivity ($\in^*$) of a material is described in equation 1 as the sum of its permittivity, $\in$, and the product of the imaginary number, i, with the conductivity of the material, σ, over the angular frequency, $\omega$ ' of the applied electric field.

$$\varepsilon^* = \varepsilon + \frac{i\sigma}{\omega} \quad \text{[Equation 1]}$$

The DEP force, FDEP, a droplet of radius (r) will experience in an electric field, E, is described by equation 2. Given a constant droplet size and electric field gradient, AC FDEP can be controlled as a function of activation frequency. Selective droplet sorting can then be achieved by balancing DEP forces against the other influential forces, namely hydrodynamic, gravity, and Brownian motion kinetic forces.

$$F_{DEP} = 2\pi r^3 \varepsilon_m Re\left\{\frac{\varepsilon_p^* - \varepsilon_m^*}{\varepsilon_p^* + 2\varepsilon_m^*}\right\} \nabla |\vec{E}_{RMS}|^2 \quad \text{[Equation 2]}$$

The complex permittivity of droplets as a function of frequency is expected to vary dependent on the number and length of DNA strands encapsulated within the droplets (Sheu and Sheu). For a known variation in dielectric permittivity between droplets containing amplified DNA, and droplets with no DNA, the voltage parameters and appropriate frequency selections can be made to distinguish between the different types of droplets. Presented here the primary interest is to sort droplets based on PCR amplification, but the same concept can be applied to sort droplets of varying contents which also affect their dielectric permittivity. This can include but not limited to PCR amplification, cell encapsulation, crystallization, chemical reactions and polymerizations, and other droplet streams of mixed content.

Figure 6:
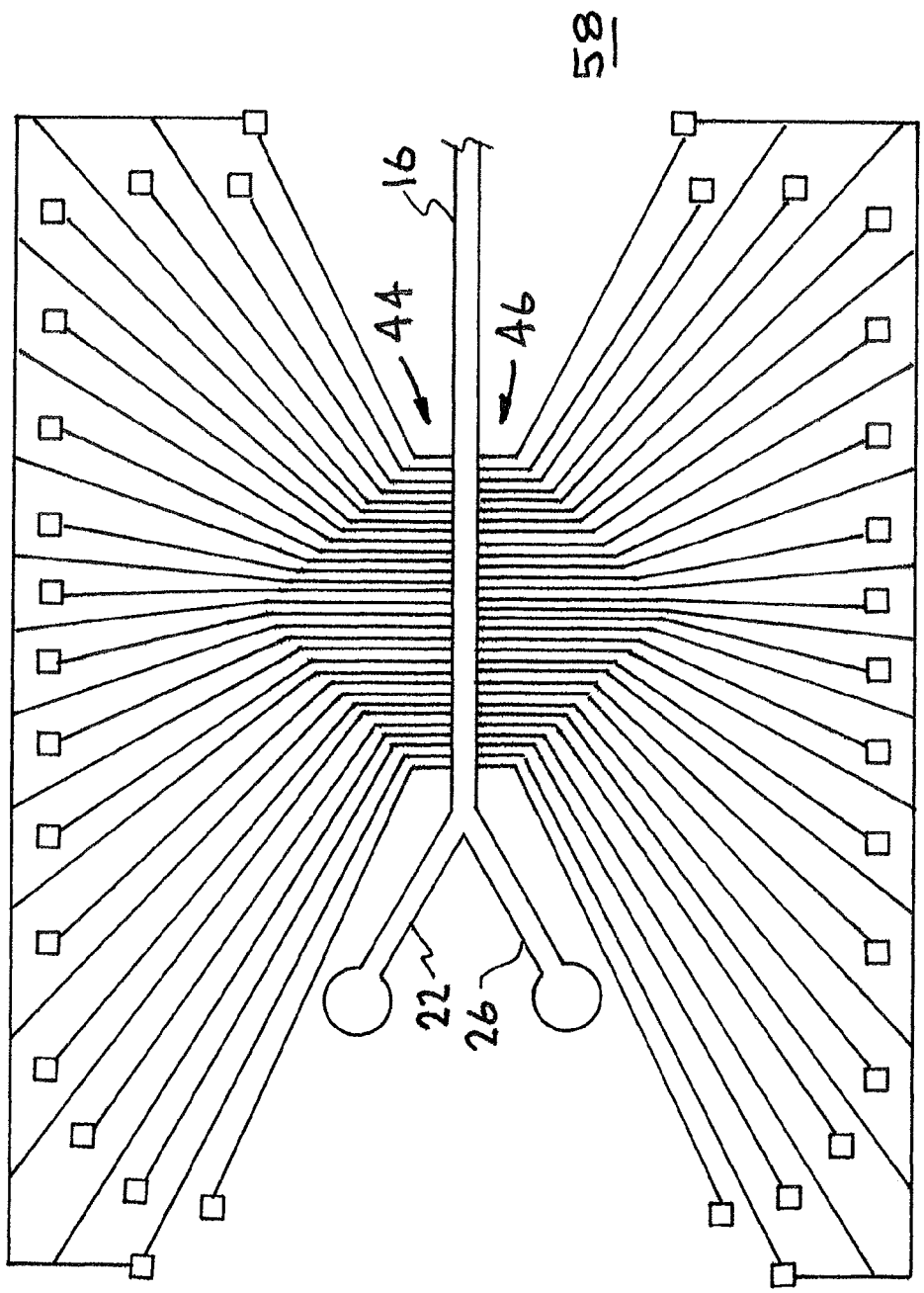
FIG. 6 illustrates electrode arrays deposited on a chip.

FIG. 6 shows the electrode arrays 44 and 46 as deposited on a chip 58. As shown the two arrays 44 and 46 straddle the channel 16. The channel 16 is 164 um wide and the two arrays 44 and 46 consisting of thirty electrodes each in a five centimeter length on either side of the channel will provide equal resistance on either side. A first mask A was used to pattern the gold electrodes and a second mask B was used to pattern the microfluidic channels in the SU-8 layer with access ports to the bond pads. In the masks, a channel width of 164 um splits into two channels of similar dimension with equal resistance on either side. Two 5 cm long array's of 30 electrodes all 84 um's long, 84 um apart, separated by a width of 200 um across the channel were used to generate the dielectrophoretic fields used to sort the droplets. The total channel distance from droplet generation to droplet sorting was 1 cm. The entire device was fabricated in SU-8 using standard lithography techniques patterned on a silicon substrate with gold electrodes and wires deposited using e-beam deposition. First the bottom of the channel is made by spinning a 10 um layer of SU-8 onto a silicon wafer substrate. 200 and 400 angstrom thin layers of Titanium and Gold layers respectively, are e-beam deposited onto the SU-8 layer. The electrodes are patterned using standard photolithography and etching techniques using mask A. Next a 60 um thick SU-8 layer composed of a dual layer spin process was deposited and patterned using Mask B. Next a turn layer of SU-8 was spun onto a 2 mm thick piece of plasma treated PDMS with cored inlet and outlet holes and soft baked. It was then placed on top of the SU-8 channel layer and heated to 100 C to allow the un-crosslinked SU-8 layer on the PDMS to seal to the SU-8 channel layer. Once all air bubbles were removed, the wafer was exposed to UV light and baked to crosslink the 2 um layer of SU-8 to the channel layer SU-8 below and the PDMS layer above.

Figure 7:
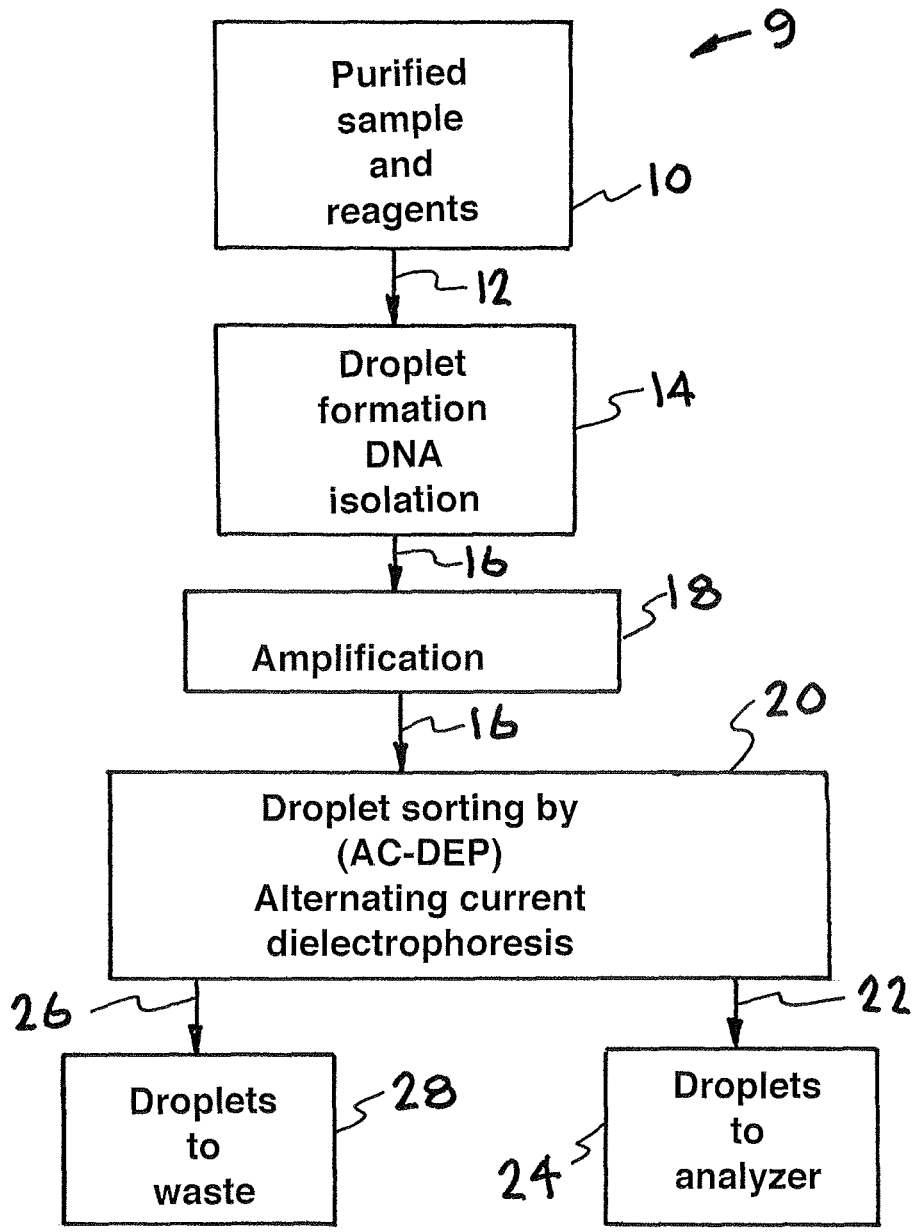
FIG. 7 is a flow chart describing the items on a chip based method and system for sorting droplets.

FIG. 7 is a flow chart describing the items on a chip based method and system for sorting droplets. The overall system is labeled 9. In step one purified sample and reagents 10 are carried by channel 12 to step two where droplet formation and DNA isolation occur. Droplets of uniform size are formed during step two and enter channel 16. The channel 16 is filled with a carrier fluid that does not mix with the droplets therefore the droplets are carried along in channel 16 spaced intervals. Some of the droplets contain DNA and some droplets are empty. The droplets proceed along the channel 16 to step three where amplification 18 takes place. After step three, amplification 18 the droplets proceed along channel 16 to step four where droplet sorting by (AC-DEP) alternating current dielectrophoresis 20. After step four the (AC-DEP) sorting the droplets of interest will go by way of channel 22 to the droplet analyzer 24 and the empty droplets will travel in channel 26 to the droplet waste 28.

Figure 8:
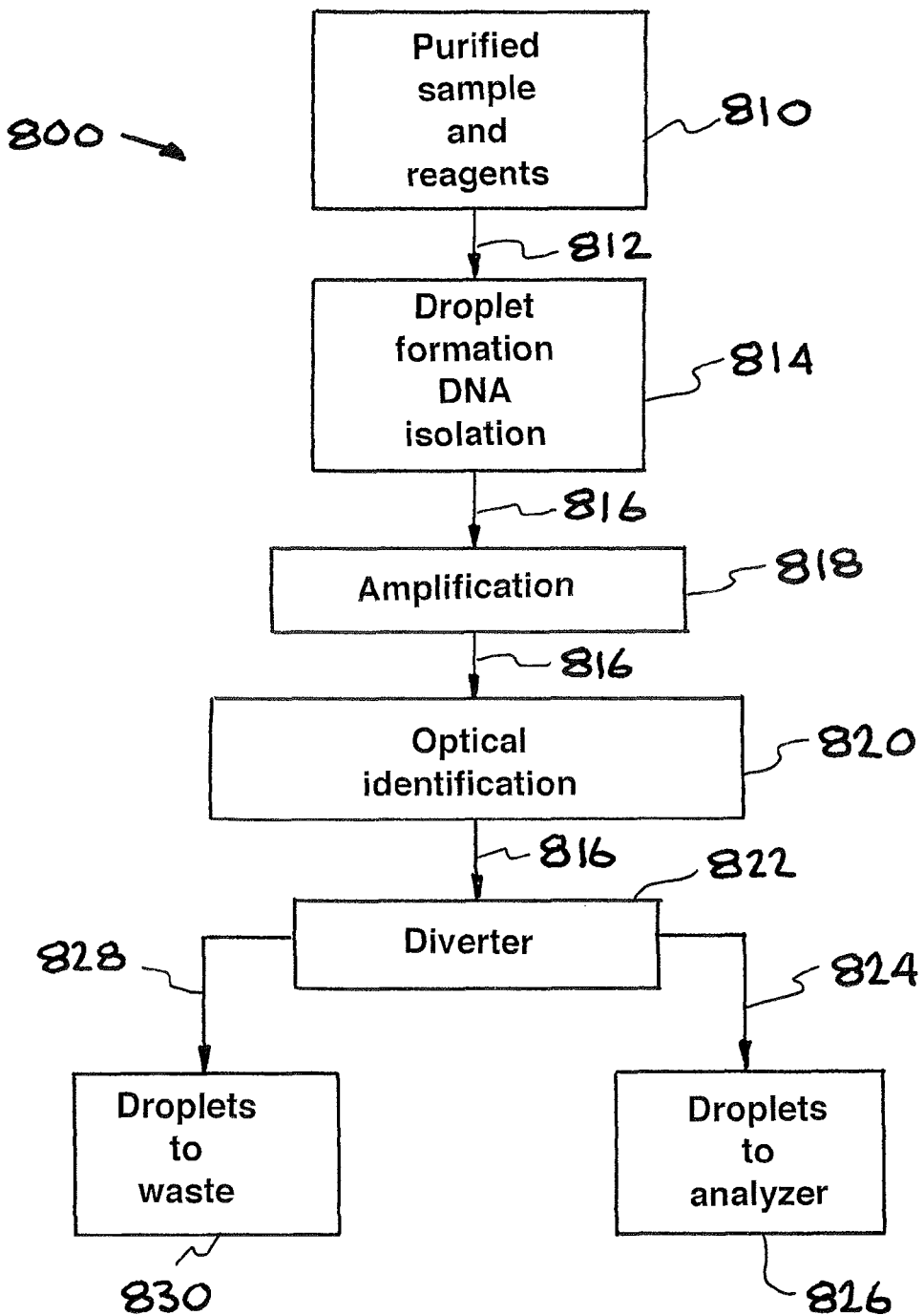
FIG. 8 is another flow chart describing the items on another embodiment of a chip based method and system for sorting droplets.

FIG. 8 is a flow chart describing the items on a chip based method and system for sorting droplets. The overall system is labeled 800. In step one purified sample and reagents 810 are carried by channel 812 to step two where droplet formation and DNA isolation occur. Droplets of uniform size are formed during step two and enter channel 816. The channel 816 is filled with a carrier fluid that does not mix with the droplets therefore the droplets are carried along in channel 816 spaced intervals. Some of the droplets contain DNA and some droplets are empty. The droplets proceed along the channel 16 to step three where amplification 818 takes place. After step three, amplification 818 the droplets proceed along channel 816 to step four where optical identification 820 occurs. After step four, diverter 822 diverts identified droplets to the appropriate channel. The droplets of interest will go by way of channel 824 to the droplet analyzer 826. The empty droplets will travel in channel 828 to the droplet waste 830.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for sorting droplets on a chip, consisting of:
 a chip;
 a microfluidic flow channel in said chip;
 a carrier fluid in said microfluidic flow channel;

a droplet maker connected to said microfluidic flow channel that provides a flow stream of said carrier fluid and said droplets in said microfluidic flow channel wherein said droplets have substantially the same diameter and wherein said droplets include first droplets containing genetic material and second droplets that do not contain said genetic material;

an amplifier connected to said microfluidic flow channel for amplifying said genetic material in said first droplets containing genetic material producing first amplified droplets containing amplified genetic material and second droplets that do not contain said genetic material;

an analyzer connected to said microfluidic flow channel;

a waste channel connected to said microfluidic flow channel; and an alternating current dielectrophoresis droplet sorter connected to said microfluidic flow channel that sorts said droplets according to said first amplified droplets containing said amplified genetic material and directs said first amplified droplets containing said amplified genetic material to said analyzer and sorts said droplets according to said second droplets that do not contain said genetic material and directs said second droplets that do not contain said genetic material to said waste channel, said alternating current dielectrophoresis droplet sorter including inter-digitated electrodes that produce a field gradient in said flow channel and on said first amplified droplets containing said amplified genetic material and said second droplets that do not contain said genetic material, and a controller connected to said inter-digitated electrodes that varies said field gradient and diverts said first amplified droplets containing said amplified genetic material to said analyzer, and diverts said second droplets that do not contain said genetic material to said waste channel.

2. An apparatus for sorting droplets on a chip, consisting of:

a chip;

a microfluidic flow channel in said chip;

a carrier fluid in said microfluidic flow channel;

a droplet maker connected to said microfluidic flow channel that provides a flow stream of said carrier fluid and said droplets in said microfluidic flow channel wherein said droplets have substantially the same diameter and wherein said droplets include first droplets containing genetic material and second droplets that do not contain said genetic material;

an amplifier connected to said microfluidic flow channel for amplifying said genetic material in said first droplets containing genetic material producing first amplified droplets containing amplified genetic material and second droplets that do not contain said genetic material;

an analyzer connected to said microfluidic flow channel;

a waste channel connected to said microfluidic flow channel; and a droplet sorter connected to said microfluidic flow channel that sorts said droplets according to said first amplified droplets containing said amplified genetic material and directs said first amplified droplets containing said amplified genetic material to said analyzer and sorts said droplets according to said second droplets that do not contain said genetic material and directs said second droplets that do not contain said genetic material to said waste channel, said droplet sorter including an optical droplet identifier connected to said microfluidic flow channel that identifies said first amplified droplets containing said amplified genetic material and said second droplets that do not contain said genetic material wherein said optical droplet identifier is a droplet identifier that includes a laser beam, and a droplet diverter connected to said optical droplet identifier that diverts said first amplified droplets containing said amplified genetic material to said analyzer, and diverts said second droplets that do not contain said genetic material to said waste channel.

* * * * *